(12) United States Patent
Shoji

(10) Patent No.: US 10,517,472 B2
(45) Date of Patent: Dec. 31, 2019

(54) ENDOSCOPE SYSTEM

(71) Applicant: HOYA CORPORATION, Tokyo (JP)

(72) Inventor: Takaaki Shoji, Tokyo (JP)

(73) Assignee: HOYA CORPORATION, Tokyo (JP)

(*) Notice: Subject to any disclaimer, the term of this patent is extended or adjusted under 35 U.S.C. 154(b) by 252 days.

(21) Appl. No.: 15/188,237

(22) Filed: Jun. 21, 2016

(65) Prior Publication Data

US 2016/0296106 A1 Oct. 13, 2016

Related U.S. Application Data

(63) Continuation of application No. PCT/JP2015/086395, filed on Dec. 25, 2015.

(30) Foreign Application Priority Data

Jan. 21, 2015 (JP) ................................. 2015-009425

(51) Int. Cl.
*A61B 1/06* (2006.01)
*A61B 1/00* (2006.01)
(Continued)

(52) U.S. Cl.
CPC ........ *A61B 1/0638* (2013.01); *A61B 1/00009* (2013.01); *A61B 1/00039* (2013.01);
(Continued)

(58) Field of Classification Search
CPC ... G06T 7/0012; G06F 3/013; A61B 1/00009; A61B 1/00039; A61B 1/0638; A61B 2017/00216
See application file for complete search history.

(56) References Cited

U.S. PATENT DOCUMENTS 5,016,282 A 5/1991 Tomono et al.
5,367,315 A * 11/1994 Pan .......................... G06F 3/013
345/156
(Continued)

FOREIGN PATENT DOCUMENTS

EP 2 422 688 A1 2/2012
JP 02-224637 A 9/1990
(Continued)

OTHER PUBLICATIONS

European Search Report issued in EP family member Patent Appl. No. 15868672.5, dated Aug. 13, 2018.
Search Report in PCT/JP2015/086395, dated Apr. 5, 2016.

*Primary Examiner* — Aaron B Fairchild
(74) *Attorney, Agent, or Firm* — Greenblum & Bernstein P.L.C.

(57) ABSTRACT

An endoscope system has an illuminator configured to illuminate an object to be observed with normal light, an image processor that generates an observed image from one field/frame worth of image-pixel signals. The image-pixel signals is read from an image sensor provided in the tip portion of a video scope, and the image processor generates a plurality of spectral images in accordance to the emission of a plurality of narrow-band light. Furthermore, the endoscope system has a detector that detects an operator's aiming spot with respect to at least the plurality of spectral images, a determiner that determines a diagnosis object area that contains the detected aiming spot, and a spectral image processor that extracts a diseased portion with spectral characteristics different from those of the other portions, among the plurality of diagnosis object areas that are defined within the plurality of spectral images.

11 Claims, 11 Drawing Sheets

(51) Int. Cl.
*G02B 23/24* (2006.01)
*G06T 7/00* (2017.01)
*H04N 5/232* (2006.01)
*A61B 1/05* (2006.01)
*A61B 17/00* (2006.01)

(52) U.S. Cl.
CPC ........ *G02B 23/2484* (2013.01); *G06T 7/0014* (2013.01); *H04N 5/23219* (2013.01); *A61B 1/00045* (2013.01); *A61B 1/05* (2013.01); *A61B 2017/00216* (2013.01); *G06T 2207/10068* (2013.01); *H04N 5/23245* (2013.01)

(56) References Cited

U.S. PATENT DOCUMENTS

| | | | |
|---|---|---|---|
| 5,818,954 A | 10/1998 | Tomono et al. | |
| 5,836,869 A * | 11/1998 | Kudo | A61B 1/00039 600/173 |
| 7,892,169 B2 | 2/2011 | Gono et al. | |
| 8,253,783 B2 | 8/2012 | Takayama | |
| 8,704,885 B2 | 4/2014 | Takayama | |
| 8,798,344 B2 | 8/2014 | Kitamura et al. | |
| 8,938,122 B2 | 1/2015 | Kanda et al. | |
| 2002/0022766 A1 * | 2/2002 | Adachi | A61B 1/00009 600/160 |
| 2006/0074307 A1 * | 4/2006 | Igarashi | A61B 1/00039 600/434 |
| 2008/0281154 A1 | 11/2008 | Gono et al. | |
| 2008/0294105 A1 | 11/2008 | Gono et al. | |
| 2011/0237883 A1 | 9/2011 | Chun | |
| 2012/0220840 A1 | 8/2012 | Morita et al. | |
| 2014/0376817 A1 | 12/2014 | Yaguchi | |
| 2015/0030254 A1 | 1/2015 | Yaguchi | |
| 2015/0145978 A1 | 5/2015 | Chiba | |
| 2015/0339817 A1 | 11/2015 | Kuriyama | |
| 2017/0150904 A1 * | 6/2017 | Park | A61B 1/00009 |

FOREIGN PATENT DOCUMENTS

| | | |
|---|---|---|
| JP | 04-017076 A | 1/1992 |
| JP | 10-290392 A | 10/1998 |
| JP | 2001-037718 A | 2/2001 |
| JP | 3607857 B2 | 10/2004 |
| JP | 2010-036017 A | 2/2010 |
| JP | 2011-005002 A | 1/2011 |
| JP | 2011005002 A * | 1/2011 |
| JP | 2011-104016 A | 6/2011 |
| JP | 2011-200517 A | 10/2011 |
| JP | 2012-050601 A | 3/2012 |
| JP | 2012-050602 A | 3/2012 |
| JP | 2012-125469 A | 7/2012 |
| JP | 2012-238041 A | 12/2012 |
| JP | 2013-202189 A | 10/2013 |
| JP | 2013-222383 A | 10/2013 |
| JP | 2013-240401 A | 12/2013 |
| JP | 2014-166298 A | 9/2014 |
| JP | 2015-173921 A | 10/2015 |
| WO | 2013/187116 A1 | 12/2013 |

* cited by examiner (A)

B (B)

ENDOSCOPE SYSTEM

CROSS REFERENCE TO RELATED APPLICATIONS

This is a continuation application of PCT Application No. PCT/JP2015/086395, filed on Dec. 25, 2015, designating the United States of America, the disclosure of which, including the specification, drawings, and claims, is incorporated herein by reference in its entirety.

The disclosure of Japanese Patent Application No. 2015-009425, filed on Jan. 21, 2015, the disclosure of which, including the specification, drawings, and claims, is incorporated herein by reference in its entirety.

BACKGROUND OF THE INVENTION

1. Field of the Invention

The present invention relates to an endoscope system that treats and/or operates on a diseased portion while photographing an object such as an organ in a body; especially, it relates to an extraction of a diseased portion from a spectral image.

2. Description of the Related Art

In an endoscope system with a function that displays a spectral image, a plurality of narrow-band light having different peak wavelengths is illuminated toward an object to be observed, and an image adequate for observation purposes can be displayed as a spectral image. For example, a narrow-band filter with spectral characteristics that have discrete (i.e., no overlapping portion) peak wavelengths, which are obtained by narrowing light-transmitting bands of R, G, and B color elements, is arranged in a light path (for example, see the Patent Document 1: JP3607857B2).

The spectral characteristics of reflected light from narrow-band light illuminating a diseased portion are different from those of reflected light from narrow-band light illuminating a normal portion. This is because densities of oxyhemoglobin and deoxyhemoglobin, which are included in blood vessels and/or substances included in biological tissue are different in a diseased portion from those of a normal portion.

Therefore, if an endoscope system generates a plurality of spectral image data by emitting different narrow-band light toward an observation object in sequence, and can detect an area in which different spectral characteristics appear due to light having a specific wavelength-band, a diseased portion can be specified. It is possible by utilizing a statistical analysis such as a multiple regression analysis.

For example, considering that there are differences between the spectral characteristics of a diseased portion and a normal portion as for the oxyhemoglobin and the deoxy hemoglobin, an endoscope system illuminates a plurality of narrow-band light in a range from 5 nm to 800 nm in sequence, and carries out a multiple regression analysis for a plurality of spectral images that are generated by emitting the plurality of narrow-band light. Component ratios (contribution ratio) of oxy hemoglobin and deoxy hemoglobin are specified in each pixel by using the multiple regression analysis, thus an observed image that emphasizes a diseased portion can be displayed (see the Patent Document 2: JP2013-240401A).

When acquiring a plurality of spectral images and specifying a diseased portion, if it is impossible to capture images of the same area, differences among spectral characteristics in each pixel cannot be detected precisely. However, it is difficult to continuously capture the same spot endoscope work when an operator must keep holding a scope, and differences in a photographed area occur between the pluralities of spectral images. Consequently, a diseased portion may be extracted erroneously.

Therefore, it is required to extract a diseased portion precisely based on a plurality of spectral images even if a photographed area varies while working with an endoscope.

SUMMARY OF THE INVENTION

An endoscope system according to the present invention has an illuminator configured to illuminate an object to be observed with normal light, and an image processor that generates an observed image from one frame/field worth of image-pixel signals that are read from an image sensor provided in the tip portion of a video scope. The illuminator is capable of emitting a plurality of narrow-band light having different peak wavelengths, respectively. For example, the illuminator is capable of switching between an emission of the normal light and an emission of the plurality of narrow-band light in accordance to a switch of an observation mode. Also, the image processor can generate a plurality of images (hereinafter, called "spectral images") from image signals that are generated in accordance to the emission of the plurality of narrow-band light.

Furthermore, the endoscope system has a detector that detects an operator's aiming spot with respect to at least the plurality of spectral images, a determiner that determines a diagnosis object area that contains the detected aiming spot, and a spectral image processor that extracts a diseased portion with spectral characteristics different from those of the other portions, among the plurality of diagnosis object areas that are defined within the plurality of spectral images.

The spectral image processor may extract a diseased portion by performing a spectral analysis and so on. For example, the spectral image processor may use multiple regression analysis. The image processor generates a diagnosis image that distinguishes the diseased portion from the other image portions. For example, the image processor may display a diagnosis image such that a diseased portion is distinguished form from the other portion in an observed image generated by normal light, and the image processor may generate an image by compositing spectral images as a diagnosis image.

An apparatus for processing an image, according to another aspects of the present invention, has a detector that detects an operator's aiming spot with respect to a plurality of spectral images, the plurality of spectral images being acquired based on a plurality of narrow-band light having different peak wavelengths, respectively, a determiner that determines a diagnosis object area that contains the detected aiming spot with respect to the plurality of spectral images, and a spectral image processor that generates a diagnosis image that distinguishes a diseased portion from the other image portions, the diseased portion having spectral characteristics different from those of the other portions among the plurality of diagnosis object areas that are defined within the plurality of spectral images.

Also, a method for processing a spectral image in an endoscope system, according to another aspects of the present invention, includes: a) detecting an operator's aiming spot with respect to at least a plurality of spectral images, the plurality of spectral images being acquired by emitting a plurality of narrow-band light having different peak wavelengths, respectively, in sequence; b) determining a diagnosis object area that contains the detected aiming spot with respect to the plurality of spectral images; and c) generating a diagnosis image that distinguishes a diseased portion from the other image portions, the diseased portion having spectral characteristics different from those of the other portions among the plurality of diagnosis object areas that are defined within the plurality of spectral images. Furthermore, a program that is stored in a computer-readable medium can be provided, and the program has a first step that detects an operator's aiming spot with respect to at least a plurality of spectral images, the plurality of spectral images being acquired by emitting a plurality of narrow-band light having different peak wavelengths, respectively, in sequence; a second step that determines a diagnosis object area that contains the detected aiming spot with respect to the plurality of spectral images; and a third step that generates a diagnosis image that distinguishes a diseased portion from the other image portions, the diseased portion having spectral characteristics different from those of the other portions among the plurality of diagnosis object areas that are defined within the plurality of spectral images.

On the other hand, an endoscope system, according to another aspects of the present invention, has an illuminator that is capable of emitting normal light and a plurality of narrow-band light having different peak wavelengths, respectively, toward an object to be observed, an image processor that generates an observed image on the basis of one field/frame worth of image-pixel signals, the image-pixel signals being read from an image sensor provided in the tip portion of a video scope, an eye detector that detects a position of an operator's gaze on a screen of a display unit that displays an observed image, and a spectral image processor that determines a diagnosis object area that contains the detected position of the operator's gaze in each of a plurality of spectral images, the plurality of spectral images being generated based on the plurality of narrow-band light, and extracts a diseased portion that has spectral characteristics different from those of the other portions, the image processor generating a diagnosis image that distinguishes the diseased portion from the other image portions.

A video processor in an endoscope system, according to another aspects of the present invention, has an illuminator that is capable of emitting normal light and a plurality of narrow-band light having different peak wavelengths, respectively, toward an object to be observed, an image processor that generates an observed image on the basis of one field/frame worth of image-pixel signals, the image-pixel signals being read from an image sensor provided in the tip portion of a video scope, an eye detector that detects a position of an operator's gaze on a screen of a display unit that displays an observed image, and a spectral image processor determines a diagnosis object area that contains the detected position of the operator's gaze in each of a plurality of spectral images, the plurality of spectral images being generated based on the plurality of narrow-band light, and extracts a diseased portion that has spectral characteristics different from those of the other portions, the image processor generating a diagnosis image that distinguishes the diseased portion from the other image portions.

BRIEF DESCRIPTION OF THE DRAWINGS

The present invention will be better understood from the description of the preferred embodiments of the invention set forth below, together with the accompanying drawings, in which.

DESCRIPTION OF THE PREFERRED EMBODIMENTS

Hereinafter, an electronic endoscope apparatus according to the present embodiments is explained with reference to Drawings.

Figure 1:
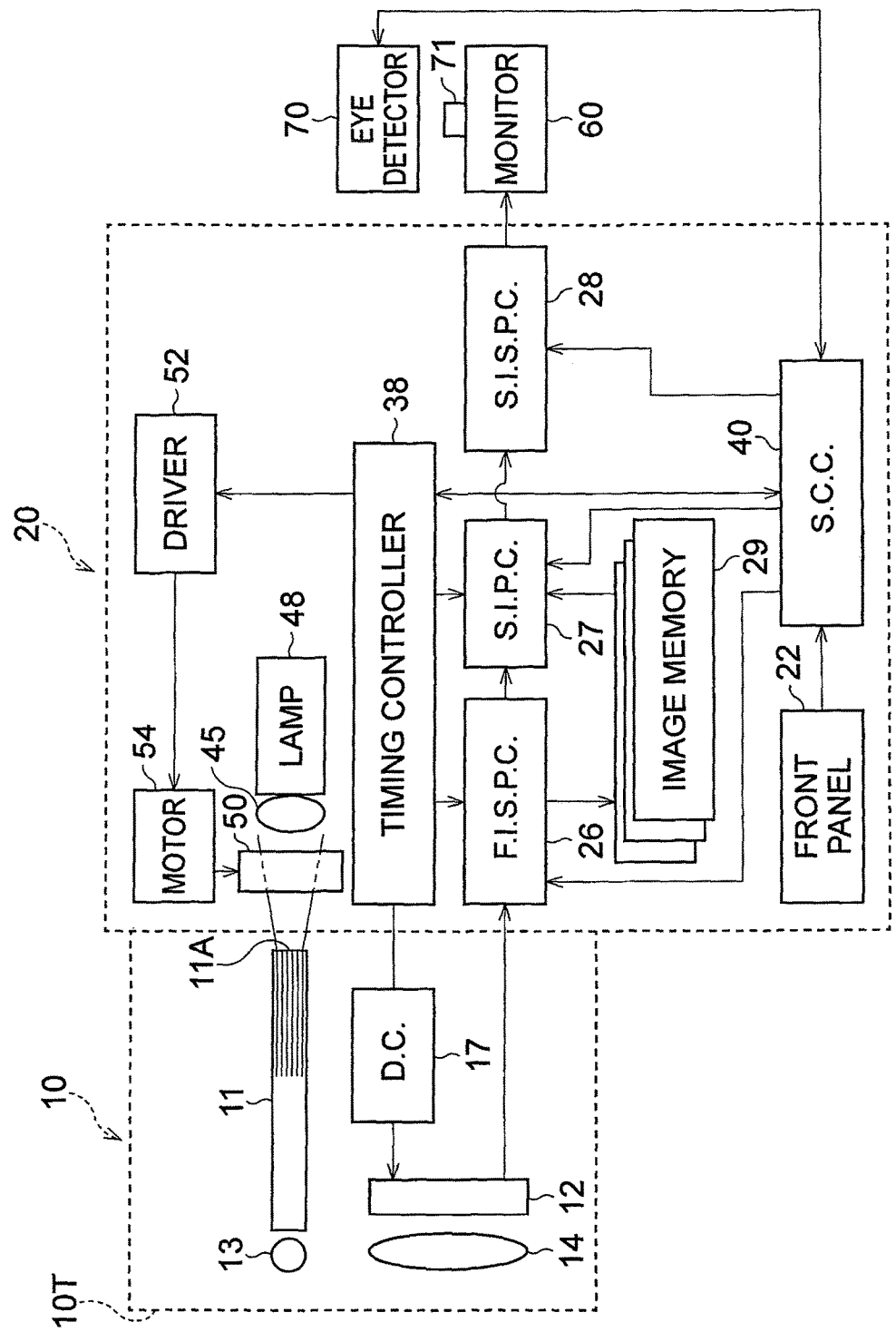
FIG. 1 is a block diagram of an endoscope system according to the first embodiment.

FIG. 1 is a block diagram of an endoscope system according to the first embodiment.

An endoscope system is equipped with an endoscope apparatus having a video scope 10 and a video processor 20, and an eye detector 70 having a camera 71. The video scope 10 is detachably connected to the video processor 20 and a monitor 60 is connected to the video processor 20.

The video processor 20 is equipped with a lamp 48 such as a xenon lamp, and the lamp 48 is driven by a lamp driver (not shown). White light (normal light) having a broadband of wavelengths is emitted from the lamp 48 and enters an incident surface 11A of a light guide 11 that is provided in the video scope 10. The white light passes through the light guide 11, and exits from the tip portion 10T of the video scope 10 toward an object (observation object) via a diffusion lens 13 to illuminate the object. A stop (not shown) is provided between the light guide 11 and the lamp 48 and an amount of illumination light is adjusted by opening and closing the stop.

Light reflected off the object is imaged onto an image sensor 12 by an objective lens 14 to form an object image on a light-receiving area of the image sensor 12. The image sensor 12 is driven by a driving circuit 17 and one field or frame worth's of image-pixel signals are read from the image sensor 12 at given time intervals (e.g., 1/60 seconds or 1/30 seconds).

The image sensor 12 is herein a CCD or CMOS type image sensor, and a color filter array (not shown) in which color elements such as R, G, and B or Cy, Ye, G, and Mg are arranged in a matrix is provided on the light-receiving area of the image sensor 12.

One field/frame worth of image-pixel signals read from the image sensor 12 are amplified and digitized on an initial processing circuit (not shown), and then fed to the video processor 20. In a first image signal-processing circuit 26 of the video processor 20, a series of digital image-pixel signals are subjected to image signal-processing such as a white balance process, a gamma correction process, etc. Thus, color image signals based on normal light, i.e., an observed image, are generated.

The generated color image signals are fed to a secondary image signal-processing circuit 28 via a spectral image-processing circuit 27. The color image signals are subjected to an edge enhancement process and a superimposing process, etc., on the secondary image signal-processing circuit 28. The processed image signals are output from the secondary image signal-processing circuit 28 to the monitor 60 so that an observed image is displayed on the monitor 60.

A system control circuit 40 including a CPU, ROM, etc., (not shown) outputs control signals to a timing controller 38, the first image-processing circuit 26, etc., and the system control circuit 40 further controls the video processor 20 while electric power of the video processor 20 is in the ON state. A program for controlling the motion of the video processor 20 is stored in the ROM in advance.

The timing controller 38 in the video processor 20 outputs clock pulse signals to electric circuits provided in the video processor 20, such as the first image signal-processing circuit 26, the driver 17, etc., to control and adjust the input/output timing of each circuit.

A disc-shaped spectral filter 50 is provided between the lamp 48 and the light guide 11. The spectral filter 50 transmits only a plurality of narrow-band light having separate peak wavelengths from one another that do not overlap with one another. Herein, the spectral filter 50 is composed of a disc in which color filter elements that have 540 nm, 555 nm, and 570 nm peak wavelengths, respectively, are arranged at even intervals. The spectral filter 50 is capable of moving from a light path to outside of the light path by using a filter driver (not shown), or vice versa.

A motor 54 rotates the spectral filter 50 by a given angle on the basis of control signals from the driver 52. The spectral filter 50 selectively directs white light or specific narrow-band light toward the light guide 11 in accordance to the rotation angle. The system control circuit 40 controls the motor 54 via the driver 52 to adjust the rotation angle of the spectral filter 50 and the rotation timing of the spectral filter 50.

A mode-setting button (not shown) is provided on a front panel 22 of the video processor 20, and the button switches a mode between a normal image observation mode that sets normal white light having a broad band of wavelengths as illumination light and a spectral image observation mode that changes from white light to narrow-band light and displays a diagnosis image that specifies a diseased portion. Furthermore, an eye-tracking mode that detects the position of an operator's gaze on a monitor-screen and displays the detected position of the gaze can be set. When diagnosing a diseased portion based on the eye tracking, an operator changes a mode to the spectral image observation mode after setting the eye-tracking mode. Note that an operator may switch between modes with an input device (not shown) provided on the video scope 10.

When the normal image observation mode is switched to the spectral image observation mode by an operator or a cooperating worker, the spectral filter 50 positioned outside of the light path is moved to a position in the light path by driving signals from the filter driver. Then, the spectral filter 50 is rotated through a given angle by the drive of the motor 54, while receiving synchronizing timing signals from the timing controller 38. Thus, three narrow-bands of light enter the light guide 11 in sequence.

The first image signal-processing circuit 26 carries out image processing on one field/frame worth of image-pixel signals for each narrow-band of light to generate an observed image based on each narrow-band of light (hereinafter, called a "spectral image"). When the spectral image observation mode is set, the spectral image-processing circuit 27 carries out spectral image processing that extracts a diseased portion from the spectral image, i.e., analyzes spectral characteristics of individual pixel data in three spectral images, and extracts pixels having spectral characteristics different from those of the other pixels and associates them with a diseased portion. Herein, a diseased portion is specified by performing multiple regression analysis on the pixel data.

After the three narrow-bands of light are emitted in sequence, the spectral filter 50 moves to the outside of the light path again to illuminate the object with normal light. The secondary image signal-processing circuit 28 carries out image processing on color image signals to distinguish the specified diseased portion from an observed image that is generated by the normal light.

The eye detector 70 detects the position of gaze of an operator that holds the video scope 10, and sends data indicating gaze position coordinates on the screen of the monitor 60 to the system control circuit 40 in the video processor 20. Herein, the eye detector 70 sends the position coordinate data while synchronizing a frame interval of image-pixel signals read from the image sensor 12. The camera 71, which is provided above the screen of the monitor 60, photographs or captures the face of an operator, and the eye detector 70 detects the position of gaze on the basis of a generated facial image.

As for the detection of the position of gaze, various eye detection methods can be applied. For example, the position of gaze can be specified by detecting a position of pupils that indicates the characteristic point of eyes or by detecting looking direction. Also, an operator may be equipped with a head-mounted type of eye detector.

The timing controller 38 in the video processor 20 outputs synchronizing signals to the eye detector 70 via the system control circuit 40. The eye detector 70 sends gaze position coordinate data in accordance to the synchronizing signals, i.e., one field/frame interval when the spectral image mode is set.

Hereinafter, a diseased portion diagnosis process based on spectral images is explained with reference to FIGS. 2 and 3.

Figure 2:
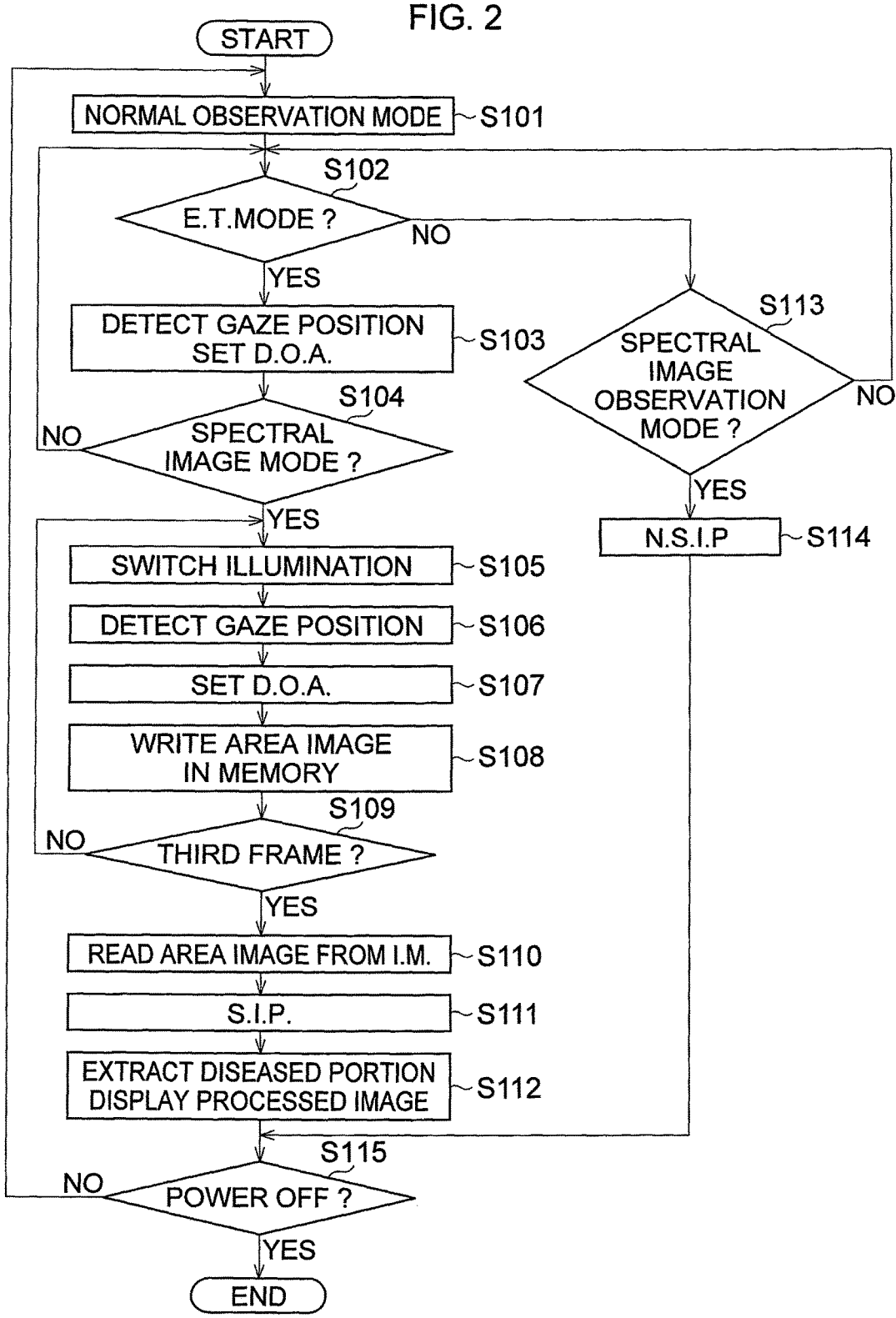
FIG. 2 is a flowchart of a spectral image process performed in the spectral image observation mode.

FIG. 2 is a flowchart of a spectral image process performed in the spectral image observation mode. FIG. 3 is a view showing the switching of illumination light and a displayed image during the state in which the eye-tracking mode is set. Note that, herein, an observed image based on normal light and a spectral image based on narrow-band light are generated in accordance to one frame interval.

In the normal observation mode, the spectral filter 50 is positioned outside of the light path to illuminate an object with normal light (S101). When the normal observation mode is changed to the spectral image observation mode in the state that the eye-tracking mode is not set, general spectral image processing is carried out (S113 and S114). The system control circuit 40 shifts the spectral filter 50 to the position in the light path and controls the rotation of the spectral filter 50 to emit three narrow bands of light in accordance to one frame interval, in sequence.

The spectral image-processing circuit 27 carries out spectral image processing that extracts a diseased portion by carrying out a spectral analysis on the basis of three frames' worth of spectral image data that are generated by the first image signal-processing circuit 26. Hereinafter, a diagnosis process for a diseased portion that is based on the spectral image processing is explained in detail.

A biological tissue to be observed has a plurality of substances that have different light-absorption characteristics, respectively, and component ratios of oxyhemoglobin and deoxyhemoglobin in a diseased portion are different from those of a normal portion because of the differences of the light-absorption characteristics (especially, in a range within 540 nm to 570 nm). Therefore, if the pixel value (luminance value) of each spectral image is regarded as an objective variable, light-absorption characteristics of oxyhemoglobin and deoxyhemoglobin in each wavelength band are regarded as explanatory variables, and the pixel data can be regarded as a sum of the explanatory variables, which means a coefficient value for each of the explanatory variables can be calculated (i.e., a parameter can be identified) by multiple regression analysis, and component ratios of oxyhemoglobin and deoxyhemoglobin can be acquired from each pixel.

However, in the spectral images obtained by emitting the three narrow bands of light, pixel information corresponding to light that is scattered in the biological tissue is also included, in addition to pixel information corresponding to light that is reflected off the biological tissue. Also, an equipment-related peculiar noise due to the characteristics of the image sensor 12, the brightness of the surrounding area of the object, etc., is included in the spectral image. Therefore, the following formula in which components of scattered light and offset components of the equipment-related peculiar noise are further included as explanatory variables, is defined.

$$\begin{pmatrix} X_1 \\ X_2 \\ X_3 \end{pmatrix} = P_1 \begin{pmatrix} a_1 \\ a_2 \\ a_3 \end{pmatrix} + P_2 \begin{pmatrix} b_1 \\ b_2 \\ b_3 \end{pmatrix} + P_3 \begin{pmatrix} c_1 \\ c_2 \\ c_3 \end{pmatrix} + P_4 \begin{pmatrix} d_1 \\ d_2 \\ d_3 \end{pmatrix} + P_5 \begin{pmatrix} 1 \\ 1 \\ 1 \end{pmatrix} \quad (1)$$

In the above formula (1), X1, X2, and X3 represent luminance data of a pixel in spectral images that are generated by light having a peak wavelength of "540 nm", light having a peak wavelength of "555 nm", and light having a peak wavelength of "570 nm", respectively, and the luminance value is represented as a logarithm. Also, a1, a2, and a3 represent light-absorption characteristics of oxyhemoglobin at wavelengths of "540 nm", "555 nm", and "570 nm", respectively, and b1, b2, and b3 represent light-absorption characteristics of deoxyhemoglobin at wavelengths of "540 nm", "555 nm", and "570 nm", respectively.

Furthermore, c1, c2, and c3 represent scattering coefficients of Rayleigh scattering at wavelengths of "540 nm", "555 nm", and "570 nm", respectively, and b1, b2, and b3 represent scattering coefficients of Mie scattering at wavelengths of "540 nm", "555 nm", and "570 nm", respectively. These coefficients are well known in the art. Note that the value of the offset coefficient P5 is a predetermined correction value as a peculiar value of the endoscope system.

By substituting a pixel value of the spectral images into the above formula 1, pixel data is decomposed to a spectrum of light absorption, spectrum of scattering coefficients, and a peculiar offset value. Since the coefficients P1 to P4 indicate contribution ratios for each spectral component, i.e., component ratios of pixel values, the coefficients P1 and P2 representing the contribution ratios of oxyhemoglobin and deoxyhemoglobin can be obtained by using multiple regression analysis to calculate the coefficients P1 to P4 in each pixel.

As described above, the component ratios (contribution ratios) of oxyhemoglobin and deoxyhemoglobin in a diseased portion are different from those in a normal portion, and a diseased portion can be specified if the ratios of the coefficients P1 and P2, i.e., the relative values of P1 and P2, can be calculated by multiple regression analysis. Therefore, the component ratios of the coefficients P1 and P2 can be obtained from the formula 1 by calculating a relative value of each coefficient when one of the coefficients P1 to P4 is set to a standard value.

The determination of a diseased portion based on a coefficient ratio for each pixel can be accomplished by using various methods. For example, a diseased portion can be specified by obtaining a histogram based on coefficient ratios of all pixels and defining pixels that have a value equal to or greater than a threshold value, respectively, as indicating a diseased portion. As for the threshold value, a threshold value may be obtained from spectral characteristics of spectral image data generated by photographing a diseased portion and a normal portion, and then stored in a memory such as a ROM.

Image edition processing is carried out by the secondary image signal-processing circuit 28 to distinguish a diseased portion from the other image portions. Concretely, it is image processing that displays pixels corresponding to a diseased portion with a specified color different from that of a normal position, with respect to an observed image that is generated after the emitted light is changed from narrow-band light to normal light. Herein, pixels corresponding to a diseased portion are displayed by a red color.

On the other hand, when it is determined that the eye-tracking mode is set be fore switching to the spectral image observation mode, the position of gaze is detected for each frame's observed image, a diagnosis object area that encompasses the position of gaze is defined, and a superimposing process that superimposes the position of gaze and the diagnosis object area on an observed image is carried out (S103).

Concretely speaking, the system control circuit 40 receives gaze position coordinate data on the monitor screen for each frame interval, and sets a diagnosis object area in which the position of gaze is at the center position of the area. In the secondary image signal-processing circuit 28, a superimposing process that displays the position of gaze and the diagnosis object area 1 on the screen of the monitor 60 is carried out under the control of the system control circuit 40.

Figure 3:
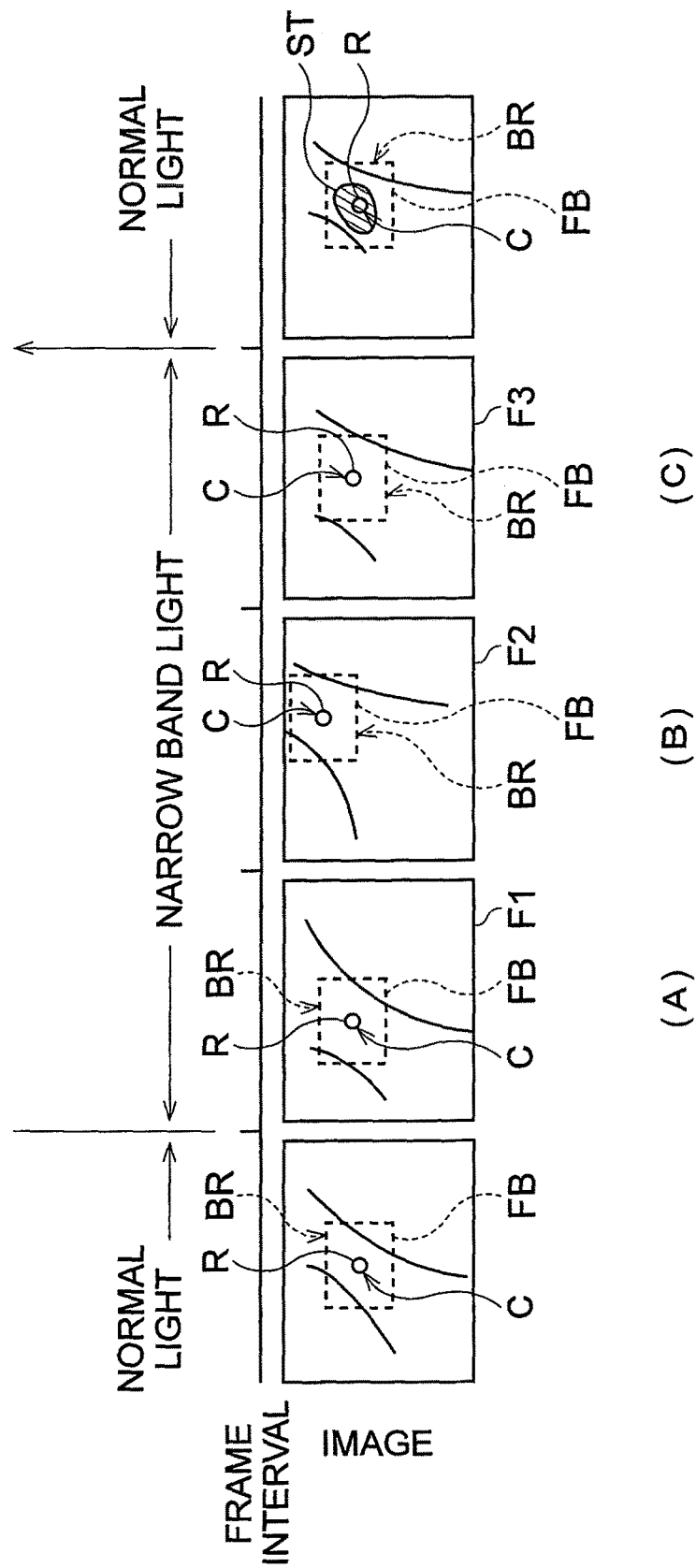
FIG. 3 is a view showing the switching of illumination light and a displayed image during the state in which the eye-tracking mode is set.

As shown in FIG. 3, the position C of a gazing direction on the screen represents the position of an intersection point of the eye-tracking line and the screen in the state that an operator gazes at suspected diseased portion (hereinafter, the position of the gaze on the screen is also designated as "C"). On the other hand, the diagnosis object area BR has a size corresponding to an area that encompasses the gaze position C, i.e., includes the diseased portion, and indicates an area that is subjected to a diagnosing process using a spectral image. Herein, the diagnosis object area BR is defined as a rectangular area in which the gaze position C is at the center point in the area.

Then, a minute circular image R that indicates the position of gaze C and a dotted-lined framed image FB that indicates the diagnosis object area BR are superimposed on the observed image. The diagnosis object area BR is set as a part of an observed image. For example, the diagnosis object area BR is set to an area less than a half-size of the observed image (screen), or an area less than one-quarter size, and so on. While an operator looks at the screen of the monitor 60, the system control circuit 40 updates the display position of the gaze position C and the diagnosis object area BR at each frame interval. Note that the size or shape of the diagnosis object area BR may be set arbitrarily.

When the normal observation mode is changed to the spectral image observation mode in the state that the eye-tracking mode is set (S104), the system control circuit 40 controls the rotation of the spectral filter 50 to illuminate an object with three narrow-bands of light in sequence (S105). The generated spectral image data are fed to the secondary image signal-processing circuit 28 via the spectral image-processing circuit 27 in sequence. Thus, three spectral images are displayed on the monitor 60 in order (see FIG. 3).

While emitting three narrow bands of light in order, the detection of the position of gaze C and the setting of the diagnosis object area BR, and the superimposing process for representing the image R indicating the position of gaze C and the frame image FB of the diagnosis object area BR are carried out for each spectral image. Then, pixel data of pixels that are in the diagnosis object area BR defined in each spectral image are output from the first image signal-processing circuit 26 and stored in the image memory 29 (S106 to S109).

While emitting narrow-band light, in order, a photographed area captured by the scope tip portion 10 is not always the same consistent area, and a photographed area could change even if an operator's holding position changes only slightly (note that the change of the photographed area is depicted exaggeratedly in FIG. 3). On the other hand, when a photographed area varies while an operator gazes at a diseased portion, the gazing position changes with the change of the photographed area. Accordingly, the position C of an operator's gaze and the position of the diagnosis object area BR also move with the movement of the position of gaze C.

In FIG. 3, a display position of the diagnosis object area BR when a spectral image (A) based on a first narrow band of light, a spectral image (B) based on a second narrow band of light, and a spectral image (C) based on a last narrow band of light are displayed, is shown. Considering that an operator continues gazing at the spot where a diagnosis object in the state that the image R indicating the position of gaze is displayed, an image of the diagnosis object area BR in each spectral image that have the position of gaze C as a center point can be regarded as an image of the substantially same place.

Namely, pixel data that have the same relative position between the three diagnosis object areas BR defined for the three spectral images can be regarded as pixel data based on the same object. Also, considering that a diseased portion occurs over some extended area, the position of a diseased portion is generally specified with precision even if a difference of pixels exists in the diagnosis object area BR.

After pixel data corresponding to the three frames' worth of diagnosis object areas BR are stored in the image memory 29, the spectral image-processing circuit 27 carries out the multiple regression analysis process for the pixel data corresponding to the diagnosis object areas BR (S110 and S111). By carrying out the multiple regression analysis, pixels regarded as a diseased portion are specified in the diagnosis object areas BR. On the other hand, the other pixel data in the diagnosis object areas BR are fed to the secondary image signal-processing circuit 28 without spectral image processing.

When a diseased portion is specified, the spectral filter 50 moves outside of the light path and an observed portion is illuminated with normal white light. Accordingly, the first image signal-processing circuit 26 generates normal color image signals. The secondary image signal-processing circuit 28 carries out a superimposing process on the basis of data from the gaze position coordinates that is fed from the eye detector 70 to superimpose the image R of the gaze position C and the frame image FB of the diagnosis object area BR onto the observed image based on the normal light.

Furthermore, the secondary image signal-processing circuit 28 carries out image processing such that a diseased portion is distinguished in the diagnosis object area BR on the basis of pixel position information of the diseased portion that is fed from the system control circuit 40 (S112). Herein, image processing that displays the diseased portion with red color is carried out. In FIG. 3, a red-colored image portion ST corresponding to a diseased portion is marked with hatching. The image processing that distinguishes the diseased portion continues for a given interval (e.g., some seconds). Steps S101 to S115 is carried out repeatedly until electric power is turned OFF.

In this way, the endoscope system 70 with the eye detector 70 emits a plurality of narrow-band light having different peak wavelengths, respectively, from the scope tip portion 10T by the spectral filter 50. On the other hand, when the eye-tracking mode is set, the position of gaze C is detected in each frame of observed images (including spectral images) that are generated by normal light and narrow-band light, and the diagnosis object areas BR are defined. Then, a diseased portion is specified by carrying out the multiple regression analysis for pixel data in the diagnosis object areas BR, and image processing is carried out to distinguish the pixels of the diseased portion.

By defining a diagnosis object area BR in accordance to the position of gaze C, images corresponding to the same portion of an object can be matched among the spectral images even if a photographed area is changed during the spectral image observation mode, which prevents an erroneous specification of a diseased portion. Also, since the position coordinate data of a gaze is detected at each field/frame interval, a diagnosis object area BR in each spectral image can always be caught. Furthermore, since spectral image-processing is carried out only for diagnosis object areas BR, the calculation speed can be improved.

Since the image R of the position of gaze C and the frame image FB of the diagnosis object area BR are continuously displayed before and after the change from the normal image observation mode to the spectral image observation mode, it is easy for an operator to fix a photographed area immediately after the change to the spectral image observation mode, and an operator can respond instantaneously and adjust the position of gaze even if a photographed area is changed slightly during the emission of the narrow-band light.

On the other hand, when the spectral image observation mode is automatically switched to the normal observation mode, image processing for specifying a diseased portion is performed on the basis of the normal image, not the spectral image, so that an operator can diagnose a diseased portion on a natural colored observed image.

As for the display of the diagnosis object area BR, an image indicating the area may be displayed only before the modes are switched, or else the display of the diagnosis object area BR may be erased after the spectral image observation mode is switched to the normal observation mode. Also, only an image that indicates the position of gaze may be displayed, while a diagnosis object area BR is not displayed before and after modes are switched. The display of the position of gaze may be started after a mode-switching operation is performed by an operator, or the position of gaze may be displayed until the emission of narrow-band light is finished and then erased when displaying a diagnosis image.

Image processing that detects pixels corresponding to a diseased portion by using spectral analysis may not be performed, but pixels may be decomposed into absorption characteristic components and scattering characteristic components by using the above formula (1). A spectral image may be composed on the basis of only the absorption characteristic components, and the composed image may be displayed on the diagnosis object area. Since the pixel value of each pixel in this diagnosis image is a sum of spectral vales, an operator can recognize a diseased portion on the screen.

Spectral images may be displayed over an interval longer than one frame interval in sequence, and the detection timing of the position of gaze may be adjusted in accordance to a display interval of the spectral images. A diagnosis image that indicates a diagnosis result may be displayed with a still image (freezing image). For example, the above composed image of the diagnosis object area may be displayed on the screen as a still image with an observed image of a moving image. Furthermore, normal light and narrow-band light may be emitted alternately while emitting a series of narrow-band light, and only a normal observation image may be displayed during such an intermittent sequence of emitting narrow-band light.

As for the spectral image processing, a diseased portion may be specified by a method other than the above-described multiple regression analysis. For example, a multiple regression analysis with a non-load high speed value, a linear regression analysis such as a least-squares method, or a Newton's method, a quasi-Newton's method, a conjugate gradient method, a damped squares method, and so on may be used.

As for the emission of narrow band light toward an object to be observed, a spectral filter having an opening portion may be rotated in the light path to respond when the mode is switched. Also, a member other than a spectral filter may be applied in place of a spectral filter. For example, a Fabry-Pero type optical device may be applied, and a laser that emits narrow-band light may also be applied.

Next, an endoscope system according to the second embodiment is explained with reference to FIGS. 4 to 8. In the second embodiment, an indicator for detecting the position of gaze is mounted on the head of an operator, in place of direct detection of the position of gaze.

Figure 4:
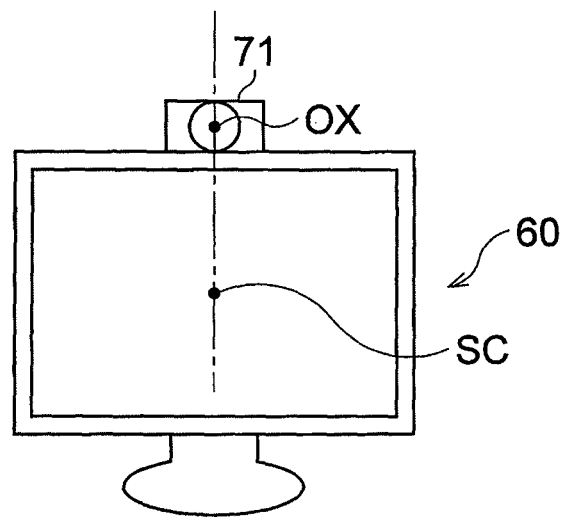
FIG. 4 is a view showing a mounted position of an imaging device.
Figure 5:
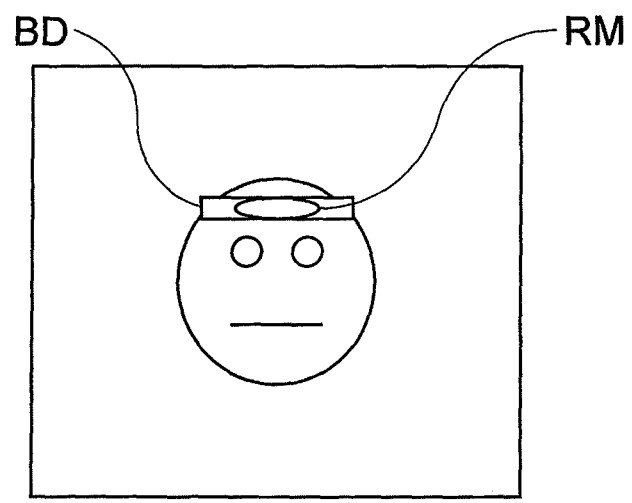
FIG. 5 is a view showing an indicator attached to the head of an operator.

FIG. 4 is a view showing a mounted position of an imaging device. FIG. 5 is a view showing an indicator attached to the head of an operator.

Similar to the first embodiment, the camera 71 is mounted on the central position of the upper portion on the monitor 60 such that an optical axis OX of the camera 71 and the center position SC on the screen are on the same line. On the other hand, a fluorescent substance RM is applied to a band BD, which is wound around the operator's head. An applied range of the fluorescent substance RM corresponds to the width of the operator's eyes and the substance RM is applied to the band BD so as to be parallel to the eyes.

The eye detector 70 detects the position of the fluorescent substance RM from a facial image generated by photographing an operator's face, and calculates the position of gaze. Herein, the position of substance RM is detected from a facial image generated when an operator gazes at a specific position on the screen, and the position of gaze is calculated from the distance between the substance RM and the operator's eyes. Therefore, a calibration process is carried out before a diagnosis of a diseased portion that utilizes a spectral image.

Figure 6:
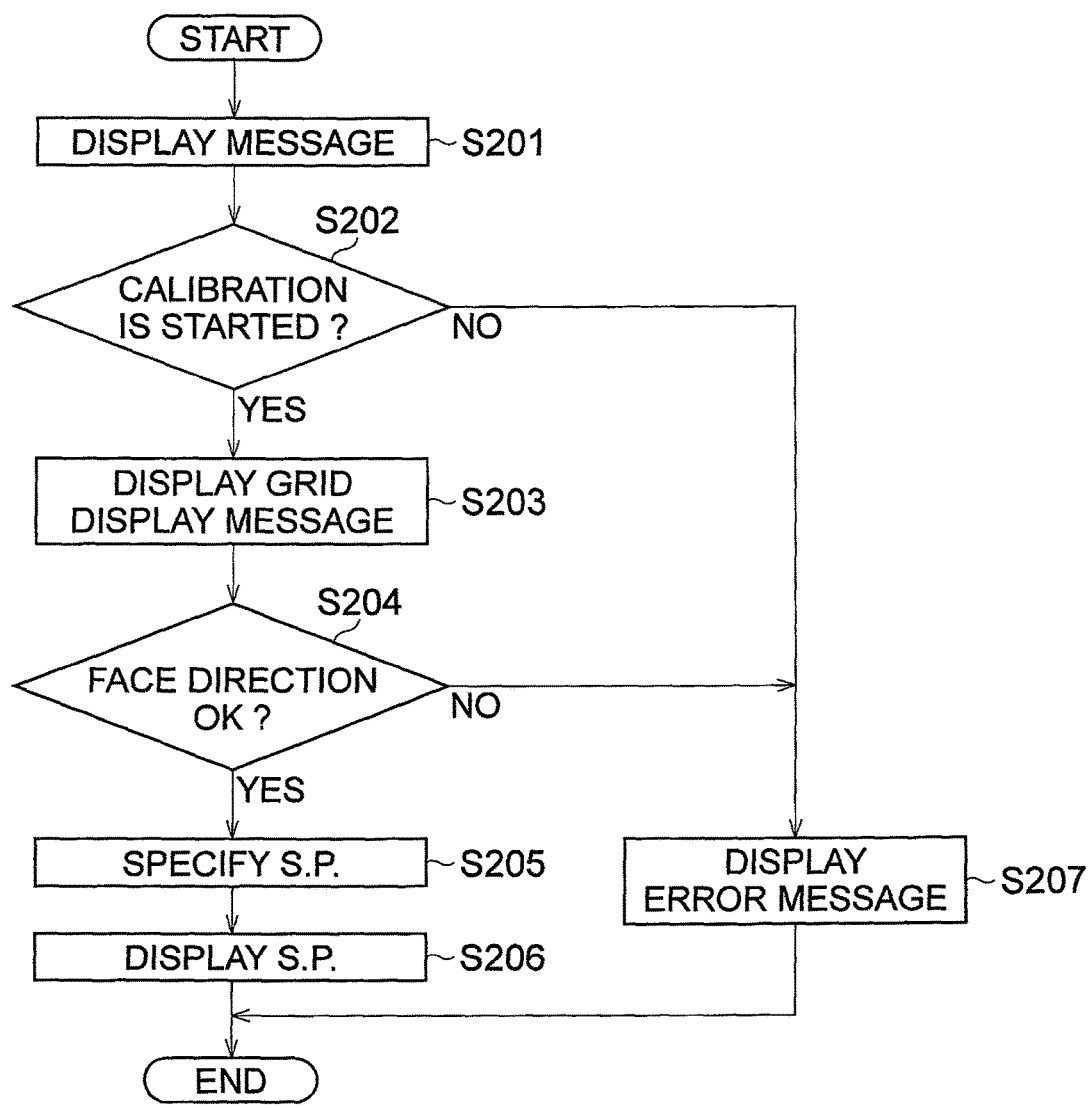
FIG. 6 is a view showing a calibration process carried out by the eye detector.
Figure 7:
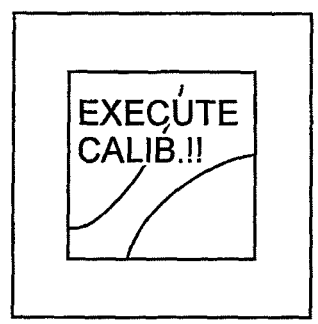
FIG. 7 is a view showing a display screen in a calibration process.
Figure 7:
Figure 7:
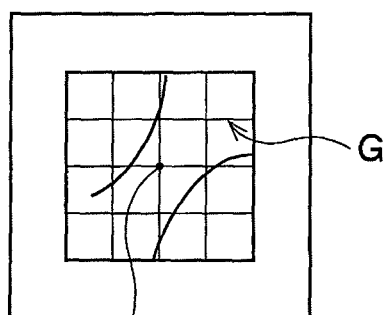
Figure 7:
Figure 7:
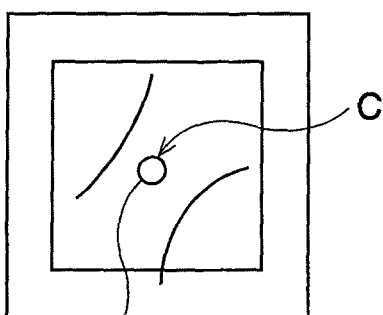

FIG. 6 is a view showing a calibration process carried out by the eye detector. FIG. 7 is a view showing a display screen in a calibration process.

When electric power of the video processor 20 is turned on, as shown in FIG. 7(A), a message indicating execution of a calibration process to an operator is displayed (S201). When another operator without a band BD operates a calibration button (not shown) provided on the front panel 22 on the video processor 20, as shown in FIG. 7(B), the system control circuit 40 controls the secondary image signal-processing circuit 28 to superimpose a grid G and a screen center point B on the screen (S202 and S203).

When an execution button provided on the front panel 22 is depressed after the direction of the face of an operator with the band BD is confirmed (S204), the position of gaze C is calculated from the position of the fluorescent substance RM on the screen, and the calculated position is defined as a standard point (S205). Then, as shown in FIG. 7(c), an image C indicating the standard point is superimposed (S206).

On the other hand, it is determined at Steps S202 and S204 that an input operation by an operator was not detected regardless of whether a given time has passed, an error message is displayed and a process is terminated (S207). When the standard point is detected once, the eye detector 70 continues detecting the standard point in each frame interval.

Figure 8:
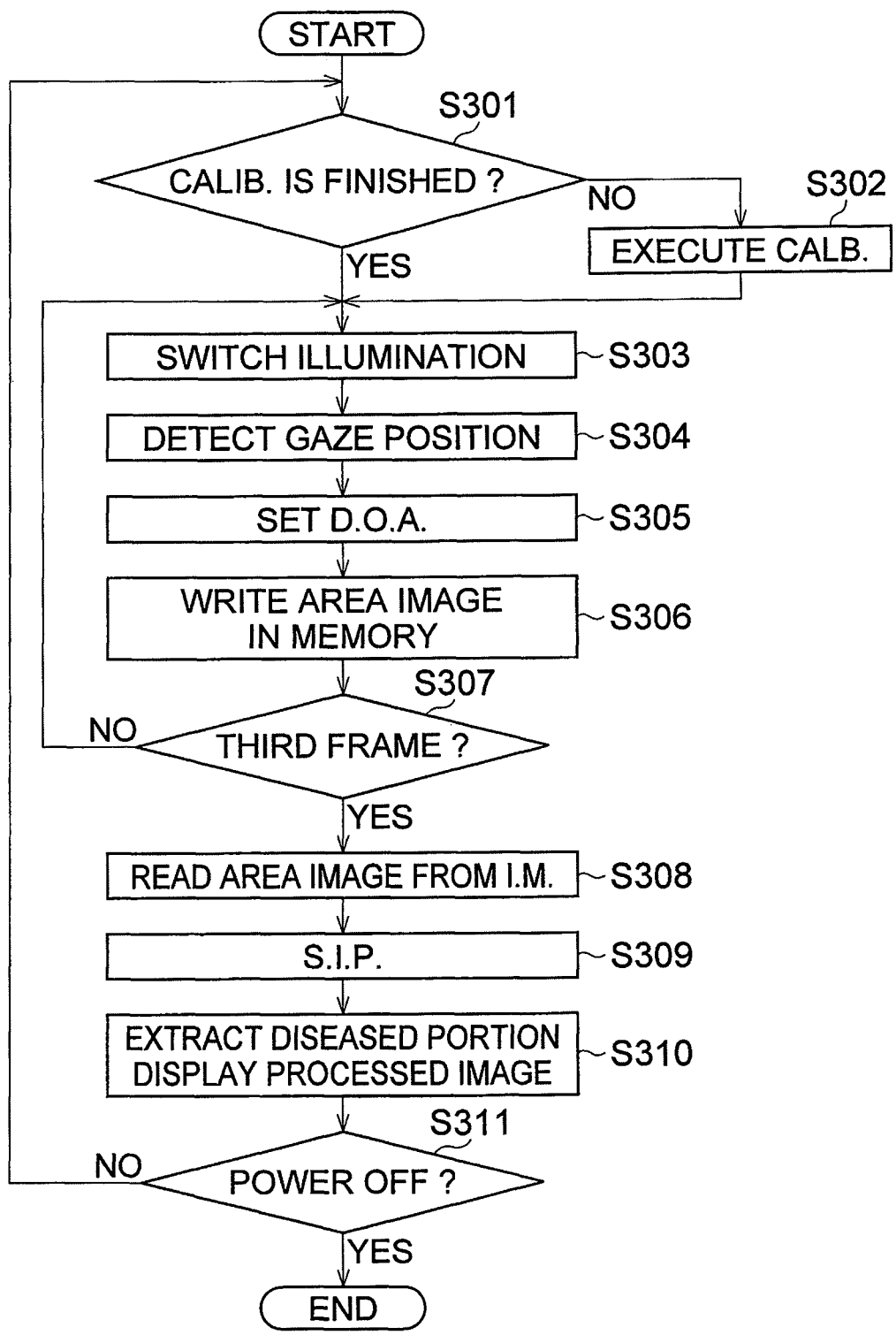
FIG. 8 is a flowchart of a spectral image processing according to the second embodiment.

FIG. 8 is a flowchart of a spectral image processing according to the second embodiment. In the second embodiment, eye tracking is carried out while the spectral image observation mode is set. When the spectral image observation mode is set, the process is started.

When it is determined that a calibration process has not yet been carried out, the calibration process shown in FIG. 6 is carried out (S301 and S302). When it is determined that the calibration process has been carried out, the spectral image processing is carried out similarly to the first embodiment. Note that, in the second embodiment, a superimposing process that displays only the standard point (the position of gaze) is carried out.

Therefore, in an interval from a time when the normal observation mode is switched to the spectral image observation mode to a time when normal light is emitted again after the emission of a plurality of narrow-band light, only the image R of the standard point is displayed. Regarding processes other than the display of the position of gaze and the diagnosis object area, the actions carried out in Steps S302 to S310 are the same as those of Steps S105 to S112 in FIG. 2.

In this way, according to the second embodiment, the position of gaze can be detected easily by using the fluorescent substance RM. Also, the position of gaze can be detected with a simple image-processing circuit. In particular, the position of gaze can be detected precisely by carrying out the calibration process before switching modes. Note that a substance other than a fluorescent substance may be applied as an indicator.

In the first and second embodiments, the eye detector equipment is independent from the video processor, however, the position of gaze may be detected in the video processor. In this case, a camera that photographs an operator's face is connected to the video processor in the endoscope system.

Next, an endoscope system according to the third embodiment is explained with reference to FIGS. 9 to 12. The third embodiment detects an adhered position of a pigment, in place of the detection of the position of gaze.

Figure 9:
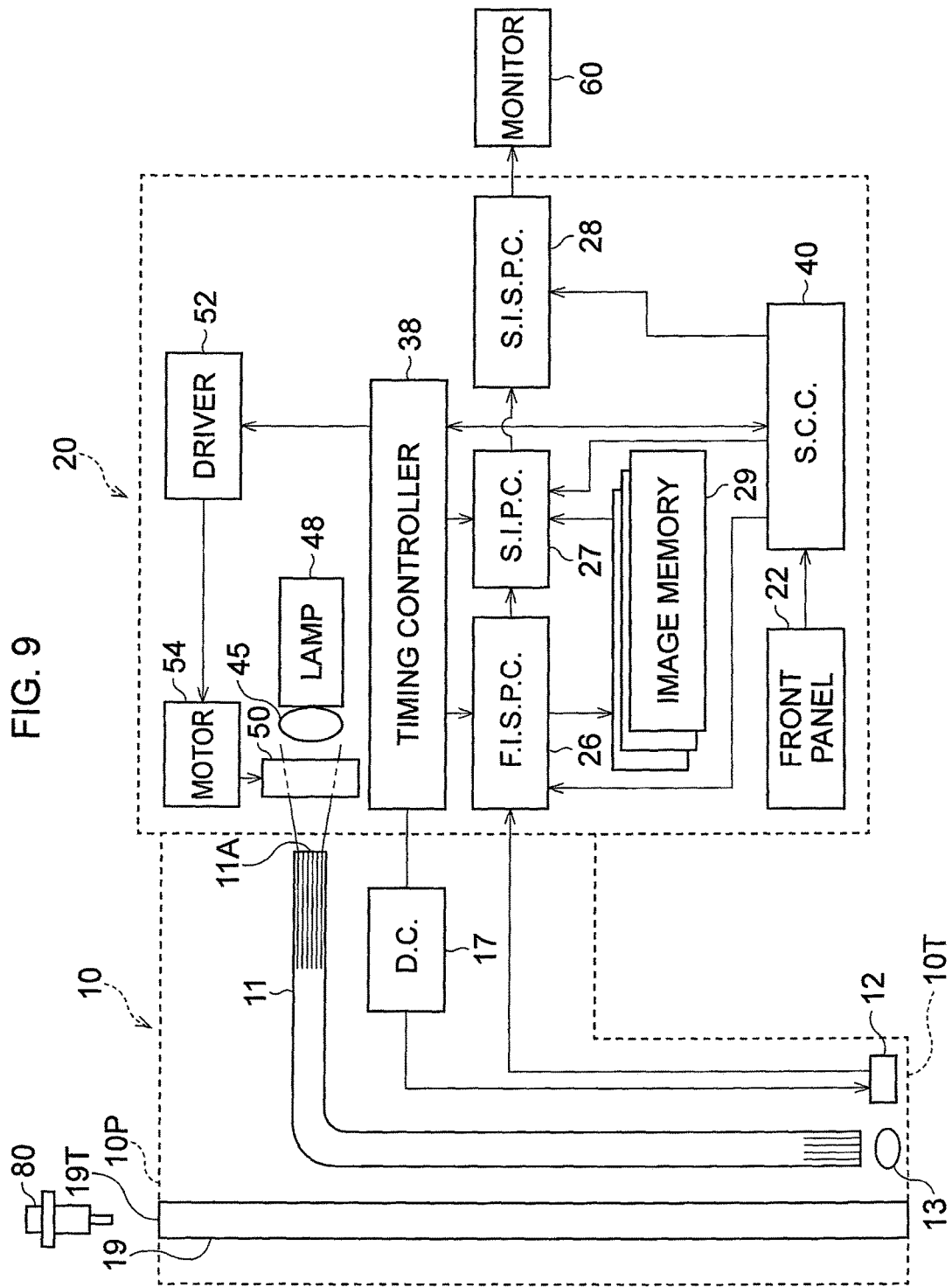
FIG. 9 is a block diagram of the endoscope system according to the third embodiment.

FIG. 9 is a block diagram of the endoscope system according to the third embodiment.

The endoscope system is equipped with the video scope 10 and the video processor 20, and furthermore the video scope 10 has a water jet function and a water-supplying tube 19 is provided between the scope operation portion 10P and the scope tip portion 10T. An operator can spout liquid toward a specific spot of an observation object by inserting a syringe 80, in which liquid such as water can be filled, into the connecting nozzle 19T and pressing the plunger of the syringe 80.

In the third embodiment, when diagnosing a diseased portion by using a spectral image, an operator fills a blue-colored indigo pigment that is used for a gastric mucosa and so on or another distinguishable pigment into the syringe 80, and spouts the pigment onto an object diagnosis portion. The system control circuit 40 detects a portion where the blue colored pigment is adhered in an observed image generated by the first image signal-processing circuit 26, and sets a diagnosis object area BR in accordance to the adhered portion. Then, when the normal image observation mode is switched to the spectral image observation mode, a diagnosis of a diseased portion is carried out on the basis of the diagnosis object area BR.

Figure 10:
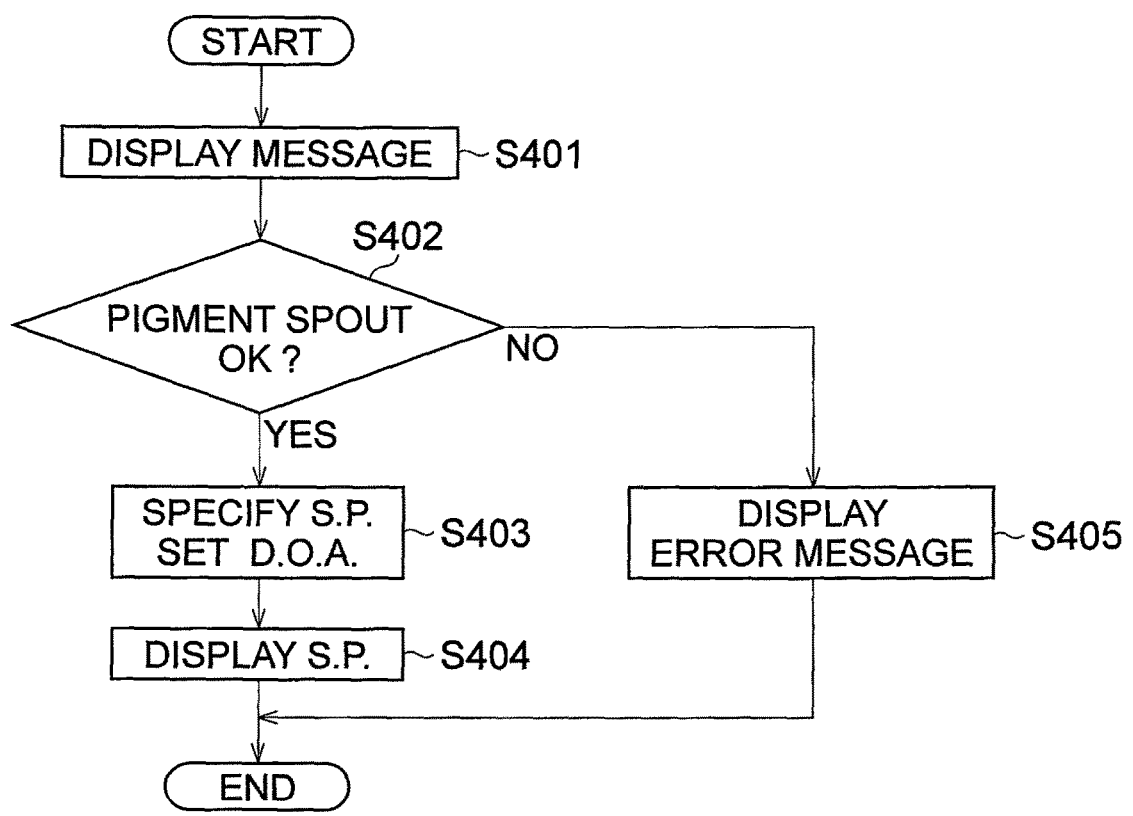
FIG. 10 is a flowchart of a process for specifying a pigment spout spot.
Figure 11:
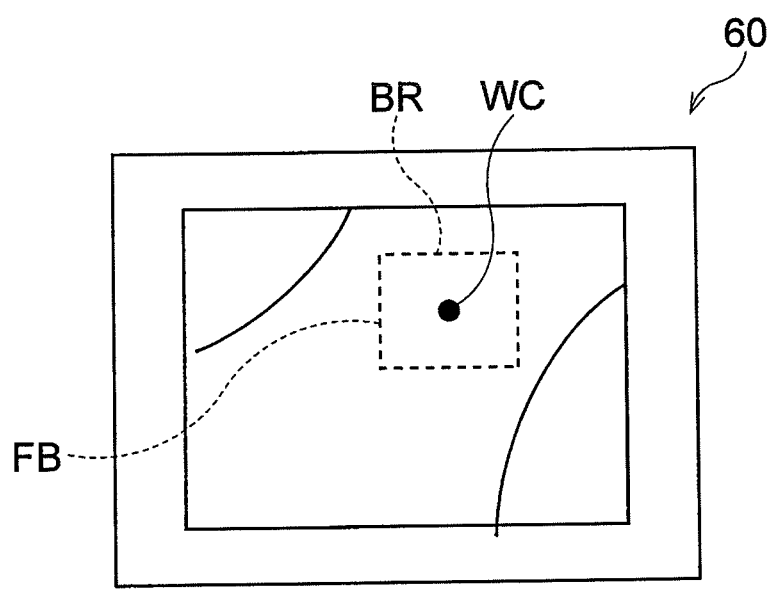
FIG. 11 is a view showing a screen in which a pigment spout spot is specified.

FIG. 10 is a flowchart of a process for specifying a pigment spout spot. FIG. 11 is a view showing a screen in which a pigment spout spot is specified.

In Step S401, a message that prompts a pigment spout is displayed on the monitor 60. An operator spouts the pigment onto a diagnosis object spot by the water jet nozzle function. At this time, the operator adjusts a depressing force for the syringe 80 so as to adhere the pigment only to the diagnosis object spot.

In Step S402, it is determined whether a pigment spout has been carried out, i.e., whether a blue-colored pigment is included in an observed image or not. When it is determined that the pigment spout has been carried out, a pixel (s) where the pigment is adhered in the observed image is specified as a standard point BC (S403). Since the size of an image area of a pigment spouted spot (blue-colored image are) generally covers a plurality of pixels, a pixel that is at a center position of the image area or is at the center of gravity of the image area may be defined as a standard point. Then, a diagnosis object area BR may be defined such that the standard point BC is the center point of the area BR.

Then, an image WC indicating the standard point BC and a frame image FB indicating the diagnosis object area BR are superimposed on an observed image (S404). After a display process is carried out for a given interval, the images WC and FB are erased. When it is determined at Step S402 that the pigment has not been detected, an error message is displayed and the process is terminated (S405).

Figure 12:
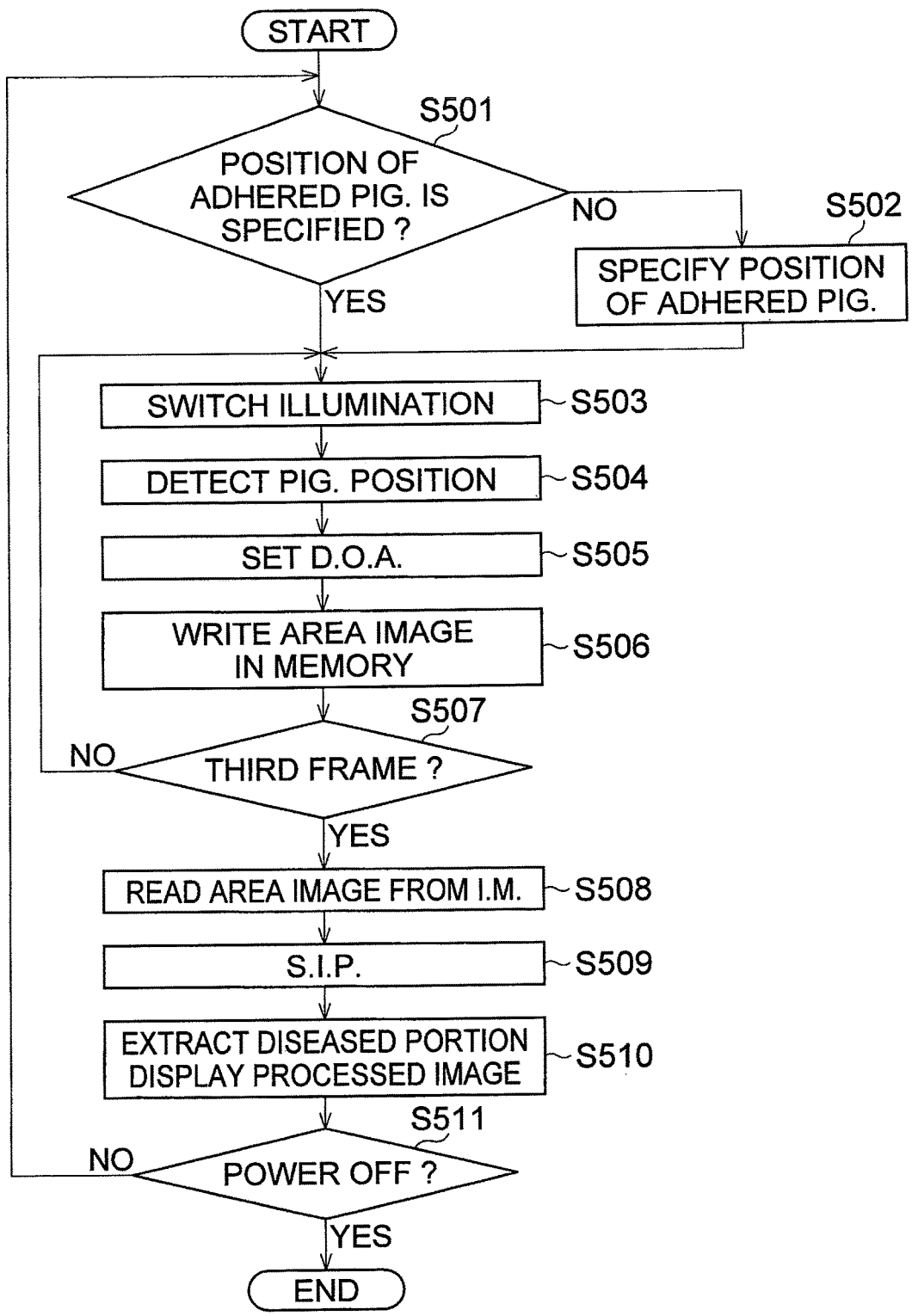
FIG. 12 is a flowchart of a spectral image processing according to the third embodiment.

FIG. 12 is a flowchart of a spectral image processing according to the third embodiment.

When it is determined that a standard point (pigment-adhered position) is not specified when the normal observation mode is changed to the spectral image observation mode, i.e., when it is determined that a pigment has not yet spouted, a process for specifying a standard point shown in FIG. 10 is carried out (S501, S502). When it is determined that a standard point is specified, three spectral images are generated by emitting narrow-band light in sequence, similarly to the first and second embodiments; and a standard point is specified in each spectral image and a diagnosis object area BR is set (S503-S507).

Since a blue colored pigment is distinguishable from the other image port ions in a spectral image, the specification of the pixel of the standard point BC means that pixel data must be obtained for the same spot. A method for specifying the standard point may be carried out as a method before the mode is changed, and spectral image processing based on a pigment spout is carried out. Note that, in the third embodiment, an image WC of the standard point and a frame image FB of the diagnosis object area BR are not displayed before and after the change to the spectral image mode. After the standard point is specified and the diagnosis object area is set, spectral image processing is carried out. When a diseased portion is extracted, a diagnosis image that distinguishes a diseased portion is displayed (S508-S511).

In this way, in the third embodiment, an image of a pigment-adhered spot is specified as a standard point by the work before the mode is switched, the diagnosis object area is set, and the specification of the standard point and the setting of the diagnosis object area are carried out for the spectral images similarly to the normal image. Thus, a diagnosis object area can be the exact same image area between spectral images.

As for the method for specifying the position of gaze or the standard position, a method without a pigment may be used because a position (sighting position) that an operator seems to be gazing at or attending to in an observed image can be detected from the observed image. For example, an image portion having relatively high light strength, a center position of an observed image, an image of a spot that is closest to the scope tip portion on an object to be observed, etc., can be detected as a standard point.

In the first to third embodiments, a diagnosis of a diseased port ion is carried out during endoscope work, however, spectral image processing may be carried out after endoscope work by storing data of diagnosis object areas in a non-volatile memory. Also, an image-processing device that diagnoses spectral images may be incorporated in a video processor or may be set independently.

An operator's aiming spot other than the position of gaze and the pigment adhered spot may be selected. Herein, "operator's aiming spot" represents a spot that an endoscope operator pays attention in an observed object and a place that is subjected to be diagnosed. As for the diagnosis object area, a given partial area or total area may be set in an observed image.

Finally, it will be understood by those skilled in the arts that the foregoing descriptions are of preferred embodiments of the device, and that various changes and modifications may be made to the present invention without departing from the spirit and scope thereof.

The invention claimed is:

1. An endoscope system comprising:
   an illuminator configured to illuminate an object to be observed with white light, said illuminator being capable of emitting a plurality of narrow-band lights having different peak wavelengths, respectively;
   an image processor that generates an observed image from one frame/field worth of image-pixel signals, the image-pixel signals being read from an image sensor provided in the tip portion of a video scope, said image processor generating a plurality of spectral images under the illumination by the plurality of narrow-band lights of the object to be observed;
a detector comprising a camera, the detector configured such that when an operator views each spectral image of the plurality of spectral images, the detector detects a respective operator's aiming spot for each spectral image of the plurality of spectral images;
a system control circuit that determines for each spectral image of the plurality of spectral images, a corresponding plurality of diagnosis object areas each within a respective spectral image of the plurality of spectral images and that contain the respective detected aiming spot as a center point; and
a spectral image processor that, after combining pixel information of the diagnosis object areas, extracts a diseased area based on spectral characteristics of the combined pixel information, said image processor generating a diagnosis image that distinguishes the diseased area from other portions of the diagnosis object areas.

2. The endoscope system according to claim 1, wherein said detector detects a position of the operator's gaze on a displayed spectral image as the operator's aiming spot, on the basis of an operator's facial image that is generated by said camera.

3. The endoscope system according to claim 1, wherein said image processor superimposes an image that indicates the operator's aiming spot on the observed image.

4. The endoscope system according to claim 1, wherein said image processor superimposes an image that indicates the diagnosis object area on the observed image.

5. An apparatus for processing an image, comprising:
a detector comprising a camera, the detector configured such that when an operator views each spectral image of a plurality of spectral images, the detector detects a respective operator's aiming spot, the plurality of spectral images being generated imager under illumination of an observable object by a plurality of narrow-band lights having different peak wavelengths;
a system control circuit that determines for each spectral image of the plurality of spectral images, a corresponding plurality of diagnosis object areas each within a respective spectral image and that contain the respected detected aiming spot as a center point; and
a spectral image processor that, after combining pixel information of the diagnosis object areas, generates a diagnosis image that distinguishes a diseased area from other portions of the diagnosis object areas, the diseased area based on spectral characteristics of the combined pixel information.

6. A method for processing a spectral image in an endoscope system, comprising:
emitting a plurality of narrow-band lights having different peak wavelengths in sequence;
detecting, via a detector having a camera, a respective operator's aiming spot for each spectral image of a plurality of spectral images, when an operator views each spectral image of the plurality of spectral images, the plurality of spectral images being acquired by observing, via an imager, an object under illumination by the plurality of narrow-band lights;
determining, via a system control circuit, for each spectral image of the plurality of spectral images, a corresponding plurality of diagnosis object areas each within a respective spectral image and that contain the respective detected aiming spot as a center point; and generating, after combining pixel information of the diagnosis object areas, a diagnosis image that distinguishes a diseased area from other portions of the diagnosis object areas, the diseased area based on spectral characteristics of the combined pixel information.

7. An endoscope system comprising:
an illuminator that is capable of emitting white light and a plurality of narrow-band lights having different peak wavelengths, respectively, toward an object to be observed;
an image processor that generates an observed image on the basis of one field/frame worth of image-pixel signals, the image-pixel signals being read from an image sensor provided in the tip portion of a video scope;
a detector comprising a camera, the detector configured to detect a position of an operator's gaze on a screen of a display that displays the observed image; and
a spectral image processor that determines a diagnosis object area that contains the detected position of the operator's gaze in each spectral image of a plurality of spectral images, the plurality of spectral images being generated under the illumination by the plurality of narrow-band lights of the object to be observed, and extracts, after combining pixel information of the diagnosis object areas, a diseased area based on spectral characteristics of the combined pixel information, said image processor generating a diagnosis image that distinguishes the diseased area from other portions of the diagnosis object areas.

8. The endoscope system according to claim 7, wherein said spectral image processor stores pixel data corresponding to each individual diagnosis object area among the plurality of diagnosis object areas in each respective spectral image temporarily, and carries out spectral image processing on the stored pixel data.

9. The endoscope system according to claim 8, wherein said spectral image processor determines an area that encompasses the position of the operator's gaze to be at the center of each diagnosis object area.

10. The endoscope system according to claim 7, wherein said detector detects the position of the operator's gaze while synchronizing with one field/frame time interval.

11. A video processor in an endoscope system, comprising:
an illuminator that is capable of emitting white light and a plurality of narrow-band lights having different peak wavelengths, respectively, toward an object to be observed;
an image processor that generates an observed image on the basis of one field/frame worth of image-pixel signals, the image-pixel signals being read from an image sensor provided in the tip portion of a video scope;
a detector that detects a position of an operator's gaze on a screen of a display that displays the observed image; and
a spectral image processor that determines a diagnosis object area that contains the detected position of the operator's gaze in each spectral image of a plurality of spectral images, the plurality of spectral images being generated under the illumination by the plurality of narrow-band lights of the object to be observed, and extracts, after combining pixel information of the diagnosis object areas, a diseased area based on spectral characteristics of the combined pixel information, said image processor generating a diagnosis image that distinguishes the diseased area from other portions of the diagnosis object areas.

* * * * *